(12) United States Patent
Hepworth et al.

(10) Patent No.: US 11,213,410 B2
(45) Date of Patent: Jan. 4, 2022

(54) DEVICE FOR MAINTAINING PATENT PARANASAL SINUS OSTIA

(71) Applicant: Audubon Technologies, LLC, Denver, CO (US)

(72) Inventors: Edward J. Hepworth, Denver, CO (US); Corey B. Kashiwa, Denver, CO (US); Steven P. Tyrrell, Erie, CO (US)

(73) Assignee: Audubon Technologies, LLC, Denver, CO (US)

( * ) Notice: Subject to any disclaimer, the term of this patent is extended or adjusted under 35 U.S.C. 154(b) by 148 days.

(21) Appl. No.: 16/361,499

(22) Filed: Mar. 22, 2019

(65) Prior Publication Data

US 2019/0380849 A1    Dec. 19, 2019

Related U.S. Application Data

(60) Continuation of application No. 14/945,717, filed on Nov. 19, 2015, now abandoned, which is a division of
(Continued)

(51) Int. Cl.
*A61F 2/82* (2013.01)
*A61F 2/18* (2006.01)
(Continued)

(52) U.S. Cl.
CPC .............. *A61F 2/82* (2013.01); *A61F 2/186* (2013.01); *A61F 2/958* (2013.01); *A61M 29/02* (2013.01);
(Continued)

(58) Field of Classification Search
CPC .. A61F 2/82; A61F 2/958; A61F 2/186; A61F 2/9517; A61F 2250/001;
(Continued)

(56) References Cited

U.S. PATENT DOCUMENTS 4,327,736 A    5/1982    Inoue
4,603,152 A    7/1986    Laurin et al.
(Continued)

FOREIGN PATENT DOCUMENTS

EP    0761251      3/1997
EP    0923913 A2   6/1999
(Continued)

OTHER PUBLICATIONS

Supplemental European Search Report issued in related European application No. EP08796750.1, dated Nov. 30, 2015, 13 pp.
(Continued)

*Primary Examiner* — Amy R Weisberg
(74) *Attorney, Agent, or Firm* — James A. Sheridan; Sheridan Law, LLC

(57) ABSTRACT

A system and method for maintaining a patent paranasal sinus ostium includes delivering a tubular element in an insertion state to the sinus ostium. The tubular element includes a proximal end, a distal end, and a center region between the proximal end and the distal end. The method includes expanding the tubular element from the insertion state to a deployment state when the tubular element is located in the sinus ostium. In the deployment state, the center region confronts the sinus ostium with an outward radial force. Other embodiments are disclosed.

20 Claims, 9 Drawing Sheets

Related U.S. Application Data application No. 14/496,763, filed on Sep. 25, 2014, now Pat. No. 9,192,490, which is a division of application No. 13/009,456, filed on Jan. 19, 2011, now abandoned, which is a division of application No. 12/181,416, filed on Jul. 29, 2008, now Pat. No. 8,303,640.

(60) Provisional application No. 61/050,827, filed on May 6, 2008, provisional application No. 60/952,606, filed on Jul. 30, 2007.

(51) Int. Cl.
*A61F 2/958* (2013.01)
*A61M 29/02* (2006.01)
*A61F 2/95* (2013.01)

(52) U.S. Cl.
CPC ..... *A61F 2/9517* (2020.05); *A61F 2210/0004* (2013.01); *A61F 2250/001* (2013.01); *A61F 2250/0004* (2013.01); *A61F 2250/0039* (2013.01); *A61F 2250/0078* (2013.01)

(58) Field of Classification Search
CPC ...... A61F 2250/0039; A61F 2250/0078; A61F 2210/0004; A61F 2250/0004; A61M 29/02
See application file for complete search history.

(56) References Cited

U.S. PATENT DOCUMENTS

| | | | |
|---|---|---|---|
| 4,650,488 A | 3/1987 | Bays et al. | |
| 4,863,444 A | 9/1989 | Biomer | |
| 4,964,850 A | 10/1990 | Bouton et al. | |
| 5,129,889 A | 7/1992 | Hahn et al. | |
| 5,234,457 A | 8/1993 | Anderson | |
| 5,246,455 A | 9/1993 | Shikani | |
| 5,313,967 A | 5/1994 | Lieber et al. | |
| 5,443,495 A | 8/1995 | Buscemi et al. | |
| 5,601,594 A * | 2/1997 | Best | A61F 5/08 606/196 |
| 5,670,161 A | 9/1997 | Healy et al. | |
| 5,693,065 A | 12/1997 | Rains, III | |
| 5,746,745 A | 5/1998 | Abele et al. | |
| 5,755,708 A | 5/1998 | Segal | |
| 5,891,133 A | 4/1999 | Murphy-Chutorian | |
| 5,968,088 A | 10/1999 | Hansen et al. | |
| 5,976,152 A | 11/1999 | Regan et al. | |
| 6,120,534 A | 9/2000 | Ruiz | |
| 6,273,910 B1 * | 8/2001 | Limon | A61F 2/91 623/1.15 |
| 6,348,067 B1 | 2/2002 | Baum et al. | |
| 6,767,346 B2 | 7/2004 | Damasco et al. | |
| 6,796,960 B2 | 9/2004 | Cioanta et al. | |
| 6,878,758 B2 | 4/2005 | Martin et al. | |
| 6,994,689 B1 | 2/2006 | Zadno-Azizi et al. | |
| 7,235,097 B2 | 6/2007 | Calisse et al. | |
| 7,241,308 B2 | 7/2007 | Andreas et al. | |
| 7,361,168 B2 | 4/2008 | Makower et al. | |
| 7,654,997 B2 | 2/2010 | Makower et al. | |
| 7,682,371 B2 | 3/2010 | Spurchise | |
| 7,771,482 B1 | 8/2010 | Karmon | |
| 7,794,494 B2 | 9/2010 | Sahatjian et al. | |
| 8,034,046 B2 | 10/2011 | Eidenschink | |
| 8,303,640 B2 | 11/2012 | Hepworth et al. | |
| 8,348,969 B2 | 1/2013 | Keith et al. | |
| 8,349,969 B2 | 1/2013 | Park et al. | |
| 8,834,468 B2 | 9/2014 | Justin | |
| 9,122,490 B2 | 11/2015 | Hepworth et al. | |
| 2002/0123765 A1 | 9/2002 | Sepetka et al. | |
| 2003/0069539 A1 | 4/2003 | Gandhi et al. | |
| 2003/0105469 A1 | 6/2003 | Karmon | |
| 2003/0135268 A1 | 7/2003 | Desai | |
| 2004/0010304 A1 | 1/2004 | Weber et al. | |
| 2004/0034405 A1 | 2/2004 | Dickson | |
| 2004/0064150 A1 | 4/2004 | Becker | |
| 2004/0116958 A1 * | 6/2004 | Gopferich | A61K 9/0092 606/199 |
| 2004/0122110 A1 | 6/2004 | MacCabee et al. | |
| 2004/0249343 A1 | 12/2004 | Cioanta | |
| 2005/0015140 A1 | 1/2005 | deBeer | |
| 2005/0166841 A1 | 8/2005 | Robida | |
| 2005/0216074 A1 * | 9/2005 | Sahatjian | C08G 18/4277 623/1.11 |
| 2005/0234453 A1 | 10/2005 | Shaolian | |
| 2005/0240147 A1 | 10/2005 | Makower et al. | |
| 2005/0288551 A1 | 12/2005 | Callister et al. | |
| 2006/0004323 A1 * | 1/2006 | Chang | A61F 2/82 604/28 |
| 2006/0095066 A1 | 5/2006 | Chang et al. | |
| 2006/0210605 A1 | 9/2006 | Chang et al. | |
| 2006/0286145 A1 | 12/2006 | Horan et al. | |
| 2007/0005094 A1 | 1/2007 | Eaton et al. | |
| 2007/0014830 A1 | 1/2007 | Tijsma et al. | |
| 2007/0027525 A1 | 2/2007 | Ben-Muvhar | |
| 2007/0073269 A1 | 3/2007 | Becker | |
| 2007/0156251 A1 | 7/2007 | Karmon | |
| 2007/0179426 A1 | 8/2007 | Selden | |
| 2007/0250105 A1 | 10/2007 | Ressemann et al. | |
| 2007/0293936 A1 | 12/2007 | Dobak | |
| 2008/0015540 A1 | 1/2008 | Muni et al. | |
| 2008/0077240 A1 | 3/2008 | Saidi | |
| 2009/0177221 A1 | 7/2009 | Kramann | |
| 2009/0198216 A1 | 8/2009 | Muni et al. | |
| 2010/0036473 A1 | 2/2010 | Roth | |
| 2010/0100170 A1 | 4/2010 | Tan et al. | |
| 2011/0021986 A1 | 1/2011 | Zamboni | |
| 2014/0243975 A1 | 8/2014 | Saidi et al. | |

FOREIGN PATENT DOCUMENTS

| | | |
|---|---|---|
| WO | 2005/122953 A2 | 12/2005 |
| WO | 2009/018248 A1 | 2/2009 |

OTHER PUBLICATIONS

Freeman, SB. Blom Ed: Frontal Sinus Stents. Laryngoscope 2000, 110:1179-82.
International Search Report and Written Opinion for PCT/US2008/071419 dated Dec. 22, 2008, 13 pp.
Benoit, CM, et al. "Combined External and Endoscopic Frontal Sinusotomy with Stent Placement: a Retrospective Review", Laryngoscope 2001, 111:1246-1249.
Bolger, WE, et al., "Catheter-Based Dialation of the Sinus Ostia: Initial Safety and Feasibility Analysis in a Cadaver Model", Am J Rhinol. May-Jun. 2006; 20(3): 290-4.
Brown, CL., et al. "Safety and Feasibility of Balloon Catheter Dilation of Paranasal Sinus Ostia: a Preliminary Investigation", Ann Otol Rhinol Laryngol. Apr. 2006. 115(4):293; discussion 300-1.
Ponsart, Biodegration of [3H]Poly(-caprolcatone) in the Presence of Active Sludge Extracts. Biomacromolecules. 2001; 2(2). 373-7.
Rains, III, MD, "Frontal Sinus Stenting", Otolaryngol Clin North Am. Feb. 2001; 34(1):101-10.
Weber, et al., "The Success of 6-Month Stenting in Endonasal Frontal Sinus Surgery", Ear Nose Throat J 2000, 79:930-932, 934, 937-938.
Supplementary Partial European Search Report for EP 08 79 6750 dated 2015-07-13, 3 pp.

\* cited by examiner

DEVICE FOR MAINTAINING PATENT PARANASAL SINUS OSTIA

REFERENCE TO PENDING PRIOR PATENT APPLICATION

This application is a continuation of prior U.S. patent application Ser. No. 14/945,717, filed Nov. 19, 2015, by Edward J. Hepworth, Corey B. Kashiwa, and Steven P. Tyrrell for DEVICE FOR MAINTAINING PATENT PARANASAL SINUS OSTIA, which is a division of prior U.S. patent application Ser. No. 14/496,763, filed Sep. 25, 2014, which is now U.S. Pat. No. 9,192,490 issued Nov. 24, 2015, by Edward J. Hepworth, Corey B. Kashiwa, and Steven P. Tyrell for DEVICE FOR MAINTAINING PATENT PARANASAL SINUS OSTIA, which in turn is a division of U.S. patent application Ser. No. 13/009,456, filed Jan. 19, 2011 by Edward J. Hepworth, Corey B. Kashiwa, and Steven P. Tyrrell for DEVICE FOR MAINTAINING PATENT PARANASAL SINUS OSTIA, which in turn is a division of U.S. patent application Ser. No. 12/181,416, filed Jul. 29, 2008, which is now U.S. Pat. No. 8,303,640 issued Nov. 6, 2012, by Edward J. Hepworth, Corey B. Kashiwa, and Steven P. Tyrrell for DEVICE FOR MAINTAINING PATENT PARANASAL SINUS OSTIA, which in turn claims the benefit of Provisional Application Ser. No. 60/952,606, filed Jul. 30, 2007, and Provisional Application Ser. No. 61/050,827, filed May 8, 2008, each of which above-identified patent applications is hereby incorporated by reference in its entirety.

FIELD OF THE INVENTION

The present invention relates to devices for treating acute and chronic inflammatory and infectious conditions of the nose and paranasal sinuses. In particular, the present invention relates to a biomedical device that is implanatable into the nose, paranasal sinuses or sinus ostium.

BACKGROUND

FIG. 1 illustrates a typical scenario that patients and physicians are faced within the case of chronic sinus disease. A diseases maxillary sinus cavity 10 of patient P has become circumferentially swollen with thickening of the lining mucosa 11. In a healthy maxillary sinus cavity 12, mucosa 13 thinly lines the cavity. Maxillary sinus cavity 12 is located below orbit 14, and frontal sinus 16 is located above orbit 14. The sphenoid sinus is located in the high posterior nasal cavity. Sinus disease is often a result of allergic or inflammatory swelling in the nasal airway 18, which frequently causes swelling in other nasal structures such as turbinates 20. This not only causes obstruction of nasal airway 18, but also the small openings, or ostia, which would normally allow for ventilation and drainage from sinus cavities 22.

Conventional methods for treating chronic sinus disease have largely been directly to surgery by an otolaryngology (ENT) physician to correct the obstructive problems in the nose and paranasal sinuses. Treatment of sinus problems has assumed a top-five position in the ranking of expense in adult care in the United States in recent years. In many, if not most, instances, surgery has developed a reputation of futility since the number of patients undergoing repeat surgical procedures is unacceptably high.

Recent advances toward minimizing sinus disease recurrence and optimizing surgical results have followed from the understanding that preservation of normal, healthy mucosa in the periphery of the surgical target site is paramount. This is particularly true in the area of the sinus ostia, where exposed bone or traumatized mucosa after sinus surgery has a robust ability to form circumferential and obstructive scar tissue which often completely closes off the sinus opening in as little as a few weeks. Combined experience with this problem has demonstrated that this obstructive process tends to occur within the first six weeks following surgery.

This timeframe for restenosis closely follows that of the now quite well understood inflammation process and the timetable of early fibrosis formation in other regions in human tissue. Taking preservation of mucosa to the ultimate degree has recently led to the usage of balloon dilational devices in the nose for expanding the sinus ostia while leaving the lining mucosa intact. However, the use of sinoplasty with a balloon catheter is of relatively limited value since it does not maintain patent paranasal ostia when obstructive or inflammatory phenomena occur after surgery.

SUMMARY

The present invention relates to a device for maintaining a patent paranasal sinus ostium. The device includes a tubular element having a proximal end, a distal end, and a center region between the proximal end and distal end. The tubular element has an insertion state and a deployment state. The tubular element is locatable in the sinus ostium when in the insertion state and expandable from the insertion state to the deployment state when located in the sinus ostium. In the deployment state, the center region confronts the sinus ostium with an outward radial force.

In other embodiments, the present invention relates to a device for delivering a stent. The device includes a handle with an actuation mechanism and a shaft having a proximal end and a distal end. The shaft proximal end is coupled to the handle. A wire extends through the shaft and has a proximal end and a distal end. The wire proximal end is operatively connected to the actuation mechanism. A first holding member is coupled to the shaft distal end and a second holding member is coupled to the first holding member at a first end and to the second holding member at a second end. The stent is positionable around the elastomeric member such that actuation of the actuation mechanism in a first direction translates the second holding member toward the first holding member to expand the elastomeric member. Actuation of the actuation mechanism in a second direction translates the second holding member away from the first holding member to contract the elastomeric member.

While multiple embodiments are disclosed, still other embodiments of the present invention will become apparent to those skilled in the art from the following detailed description, which shows and describes illustrative embodiments of the invention. According, the drawings and detailed description are to be regarded as illustrative in nature and not restrictive.

Figure 1:
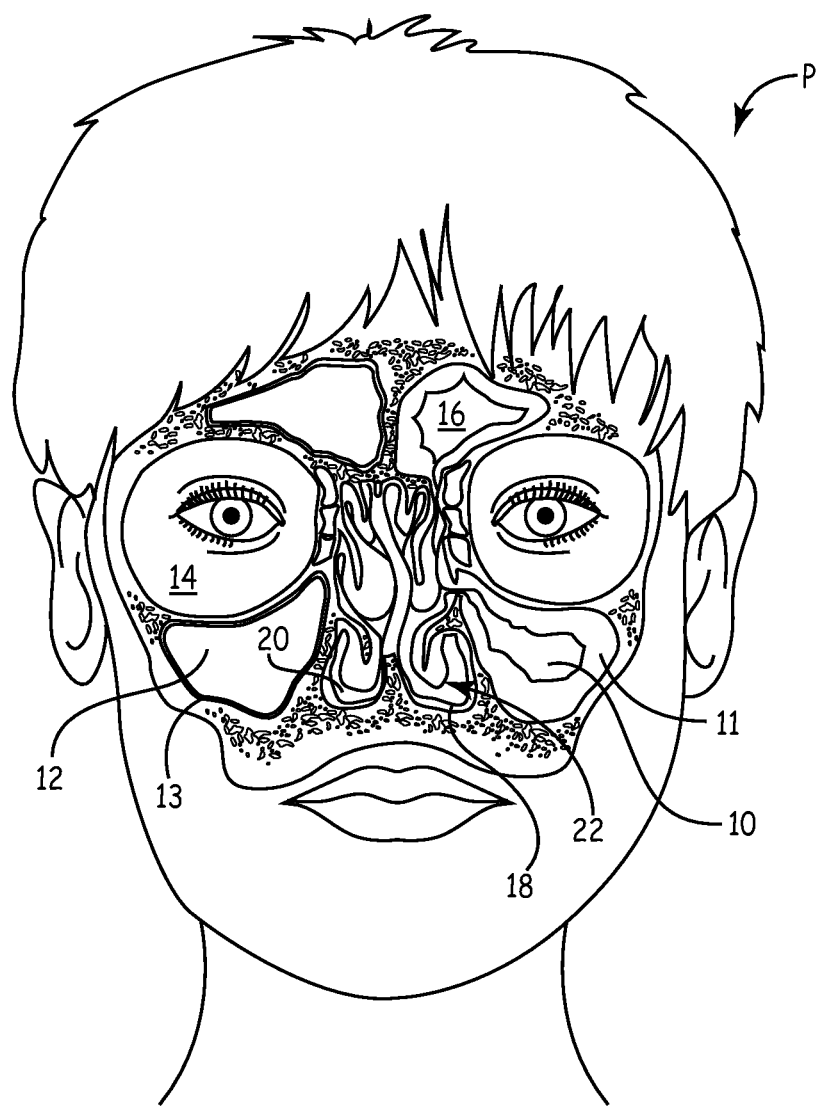
FIG. 1 is a partial cross-sectional view of a patient with chronic sinus disease, illustrating normal nasal and sinus cavities on the left side and diseased nasal and sinus cavities on the right side.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DESCRIPTION OF ILLUSTRATIVE EMBODIMENTS

Figure 2:
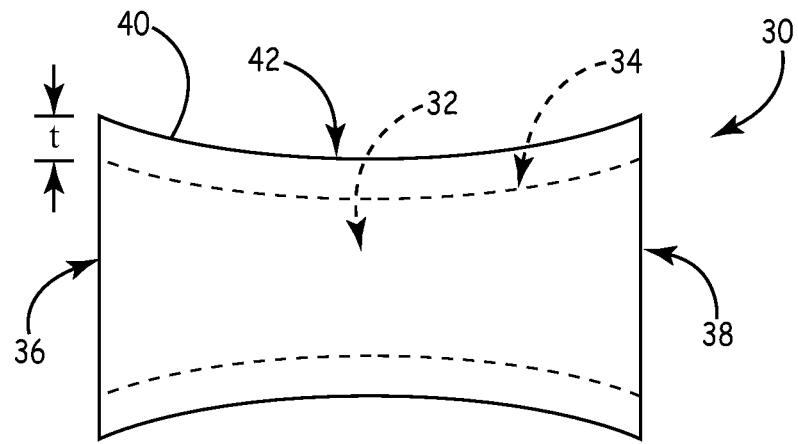
FIG. 2 is a plan view of a sinonasal stent device according to an embodiment of the present invention.

FIG. 2 is a plan view of sinonasal stent 30 according to an embodiment of the present invention. Sinonasal stent 30 includes lumen 32 defined by inner wall 34 that passes through sinonasal stent 30 between ends 36 and 38. Sinonasal stent 30 also includes outer wall 40. Wall thickness t is the distance between inner wall 34 and outer wall 40. In some embodiments, sinonasal stent 30 has a tubular shape.

When deployed, sinonasal stent 30 has a substantially hourglass shape as shown including center or waist 42 having a smaller surface-to-surface diameter than ends 36 and 38. As will be described in more detail herein, the hourglass-like shape of the deployed stent functions in the self-positioning nature of the device, and waist 42 results from expansion of ends 36 and 38 around a short ostium in the sinus bony opening.

Prior to deployment, ends 36 and 38 may have a larger starting diameter than center or waist 42. Alternatively, the diameter of sinonasal stent 30 may be substantially uniform across waist 42 and ends 36 and 38, with deployment increasing the diameter of the ends 36 and 38 more than waist 42, resulting in a post-deployment hourglass shape. The predeployment shape of the device depends upon its ultimate composition, as some component materials have a higher void fraction and compressibility than others.

To produce sinonasal stent 30, biocompatible material may be formed into a cylindrical or alternative-shaped sleeve that, when deployed over an expanding balloon or other expansile deployment device, allows sinonasal stent 30 to generate an outward radial force within the area of interest. In contrast to conventional designs, sinonasal stent 30 is not of a size smaller than the ostium or cavity at the time of insertion. Rather, the shape of sinonasal stent 30, with waist 42 having a smaller diameter than ends 36 and 38, provides constant outward radial force, and thus expansile pressure to the sinus opening, that is not afforded by a cylinder of uniform diameter. This maintains the sinus ostia in a patent (i.e., open) position. Unlike a uniform-diameter tube of silicone rubber, the tapered, bi-conical shape of sinonasal stent 30 provides increased and durable outward pressure. In some embodiments, waist 42 is comprised of a material different than the material of the remainder of stent 30 (proximate ends 36 and 38) such that the material proximate ends 36 and 38 stretches the material of waist 42 in order to produce an outward radial force on the sinus ostium.

The materials and compositions used to form sinonasal stent 30 may preferably exhibit certain biochemical properties. For example, the sinonasal stent 30 may have intrinsic antimicrobial properties, such as those described in U.S. Pat. No. 4,603,152. Further, after conformation to the ostium, the material properties of sinonasal stent 30 maintain continued centrifugal pressure on the margins of the opening to discourage restenosis. The conformable, elastic properties of sinonasal stent 30 may be accompanied by a gradual biodegradation of the material of sinonasal stent 30 which obviates the need for removal. It may also allow the timed-release of impregnated compounds for constant exposure of the sinus and nasal tissue to selective bioactive pharmaceuticals. Indwelling durability may be variable, depending upon the disease process under treatment and as determined by the selectable material of sinonasal stent 30. Several exemplary materials may be of utility in sinonasal stent 30, as listed below in Table 1. The choice of materials is based upon demonstrated relative bioinertness, retained elasticity after melting and annealing, and the possibility of porosity in the final state to allow the device to be a carrier for impregnated and releasable compounds.

TABLE 1

Primary Candidate Stent Compounds

| Compound | Young Modulus (MPa) | Melting Temp (C.) | Glass Temp (C.) | Porosity | Biologic $t^{1/2}$ (weeks) |
| --- | --- | --- | --- | --- | --- |
| Poly-ε-caprolactone | 216 | 60 | 65 | Variable | 6-10 |
| Polyhydroxy-butyrate | 70 | 55 | −15 | Variable | 24-48 |
| Poly-4-hydroxy-butyrate | 6 | 175 | 4 | 80% | 24-48 |
| Polyglycolic acid | 1.5 | 230 | Variable | Variable | 8 |
| Polyhdroxy-propionate | 1590 | 70 | 46.5 | 10% | Unknown |
| Polyhydroxy-valerate | 570 | 77 | −19 | Variable | Variable |

Polycaprolactone has been proposed as a material for a dissolvable ear tube apparatus in U.S. Pat. No. 4,650,488, and for a dissolvable epidural catheter in U.S. Pat. No.

5,129,889, and is one preferred material for sinonasal stent 30. In some embodiments, sinonasal stent 30 is comprised of a material that dissolves within about two to ten weeks. In other embodiments, sinonasal stent 30 is comprised of a material that dissolves within about one year. Several other materials may be considered for sinonasal stent 30 based upon their successful use in nasal, head, and neck surgical treatments and their demonstrated relative biocompatibility. It should be noted that each of these materials, when combined with others or when placed into the proper matrix or void fraction, exhibits the desirable properties of a sinus stent: elasticity, controlled expandability, porosity for inclusion of elutable drugs, and adequate softness for withdrawal if needed from the nasal cavity without extensive tissue damage.

Other materials may be of preferential use in certain disease states where a longer indwelling time may be needed. Some example disease states that may require longer indwelling time include severe nasal polyposis or when chronic disease states such as cystic fibrosis or inverted papilloma, a type of intranasal neoplasm, are treated. Example materials suitable for longer indwelling time include, but are not limited to, polybutyrolactone, polyglycolic acid, hyaluronic acid in resin form, poly-4-hydroxybutyrate, crosslinked hyaluronic acid, porcine collagen in resin form, methylmethacrylate, cyanoacrylate, polybutylmethacrylate, poly(L-lactide) and poly(D-lactide), polybutylmethacrylate, and polyethylene covinyl acetate.

The biochemical properties of any of the above materials allow them to be partially melted by the use of a hot-water bath or solvent prior to insertion, which will then allow them to be expanded to conform to the sinus ostium or cavity without becoming brittle, fracturing, or otherwise disintegrating. Such conformational flexibility is preferred for sinonasal stent 30 to be inserted into the nasal or sinus passages.

Sinonasal stent 30 as described allows compounds such as anti-inflammatory, antibiotics, and other immune-modulating substances to be employed in a prolonged-contact manner in the sinus tissues. In some embodiments, materials incorporated into sinonasal stent 30 allow elution or slow release of therapeutic agents useful in treating chronic sinus disease. For example, sinonasal stent 30 may be configured to include a steroid or anti-inflammatory agent including, for example, dexamethasone, triamcinolone, prednisone, prednisolone, budesonide, mometasone, fluticasone, flunisolide, zafirlukast, montelukast, and/or zileuton. Sinonasal stent 30 may also be configured to include antineoplastics or fibroblast inhibitors, including, for example, mitomycin C, 5-fluorouracil, cyclosporine, methotrexate, and/or halofuginone. In addition, sinonasal stent 30 may be configured to include antiviral compounds including, for example, cidofovir and/or podophyllin. Sinonasal stent 30 may further be configured to include antibiotics including, for example, penicillins, cephalosporins, fluroquinolones, macrolides, clindamycin, aminoglyosides, tetracycline, iodine/iodides, vancomycin, rifampin, and/or sulfa compounds. Furthermore, sinonasal stent 30 may be configured to include polyp-dehydrating medications including, for example, furosemide. Other antiscar tissue compounds and mucolytics may also be included in sinonasal stent 30, including, for example, hyaluronic acid, various detergents and surfactants, and/or acetylcysteine. It should be noted that the therapeutic agents listed are merely exemplary, and any suitable pharmacological substance may be used in conjunction with sinonasal stent 30 to treat chronic sinus disease.

Figure 3:
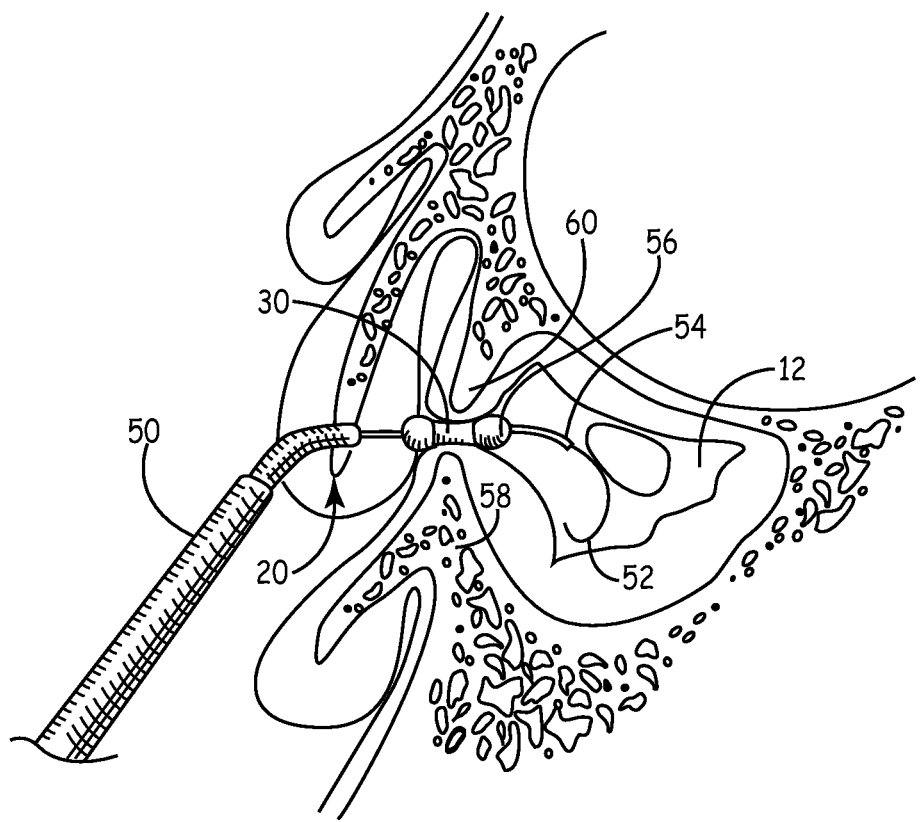
FIG. 3 is a partial cross-sectional view of a hollow directional sheath inserted into the nasal cavity for deployment of a stent device according to an embodiment of the present invention.

FIG. 3 illustrates a method and apparatus for deploying sinonasal stent 30 through the nasal cavity. In the embodiment shown, hollow directional sheath 50 is inserted into the nasal cavity using endoscopic guidance. Wire 52 is passed through sheath 50 and into maxillary sinus cavity 12 which is found lateral to middle turbinate 20 on the lateral nasal wall. This procedure may also be utilized for frontal and sphenoid sinus disease. Insertion of wire 52 is followed by passage of catheter 54. Expansile balloon or elastomeric member 56 is disposed around catheter 54 and is positioned to span sinus ostium 58 in preparation for placement of sinonasal stent 30 at the bony opening into sinus 60. This may be viewed by endoscopic examination of the nasal cavity and sinuses.

Figure 4:
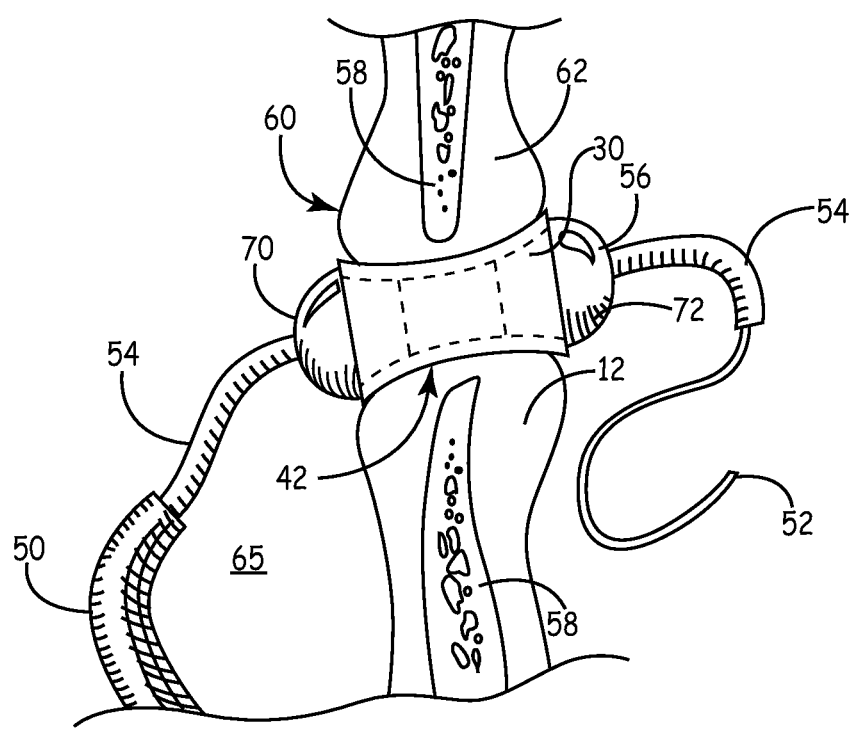
FIG. 4 is a partial cross-sectional view of the stent device expanding into position via a balloon having a waist at its center according to an embodiment of the present invention.

FIG. 4 provides further detail of guidewire 52, catheter 54, balloon 56, and sinonasal stent 30. As shown, sinonasal stent 30, which has waist 42 at its center, undergoes expansion by balloon 56 during deployment. In the embodiment shown, sinonasal stent 30, guidewire 52, catheter 54, and balloon 56 are positioned with the assistance of positioning directional sheath 50. In other embodiments, sheath 50 and wire 52 are not used to deploy the device, particularly in the case of a previously performed aggressive surgical opening of sinus 60. Sinonasal stent 30 is depicted during the process of inflation to form a self-retaining, self-positioned opening support for sinus mucosa 62 and bone of sinus ostium 58 as they heal to allow communication between sinus cavity 12 and nasal cavity 65.

Balloon 56 used in deployment of sinonasal stent 30 is an isobaric, compliant, expansion balloon. That is, as more air or fluid is delivered to balloon 56, its size increases rather than its internal pressure. This will allow the proximal segment 70 and distal segment 72 of balloon 56 to expand to dilate sinonasal stent 30 to as large a diameter as the surgeon desires, based upon the topography of the diseased sinus 60. The expanding balloon 56 will push the sinonasal stent 30 into conformity with any surface irregularities of the anatomy, resolving shortcomings of conventional cylindrical stents. A tight band, or waist, in the balloon 56 at its midlength assists in forming the hourglass shape of sinonasal stent 30, providing a means for self-positioning of balloon 56 and sinonasal stent 30. Difficult-to-reach regions of sinus 60 may be accessed with the assistance of a curved directional sheath 50 to provide angulation of catheter 54 in the direction of the target tissue, as shown in FIG. 4.

The possible adherence of sinonasal stent 30 to balloon 56 after deployment, with subsequent tearing or deformation of sinonasal stent 30 after deployment, has been investigated. A possible solution was proposed in U.S. Pat. No. 5,746,745 (incorporated herein by reference) by surface alterations in balloon 56. Surface coatings have also been proposed to release sinonasal stent 30 from balloon 56. However, the properties of the materials discussed above for sinonasal stent 30 may eliminate the need for a separation process based upon the shrinkage that may occur during cooling/hardening.

Figure 5:
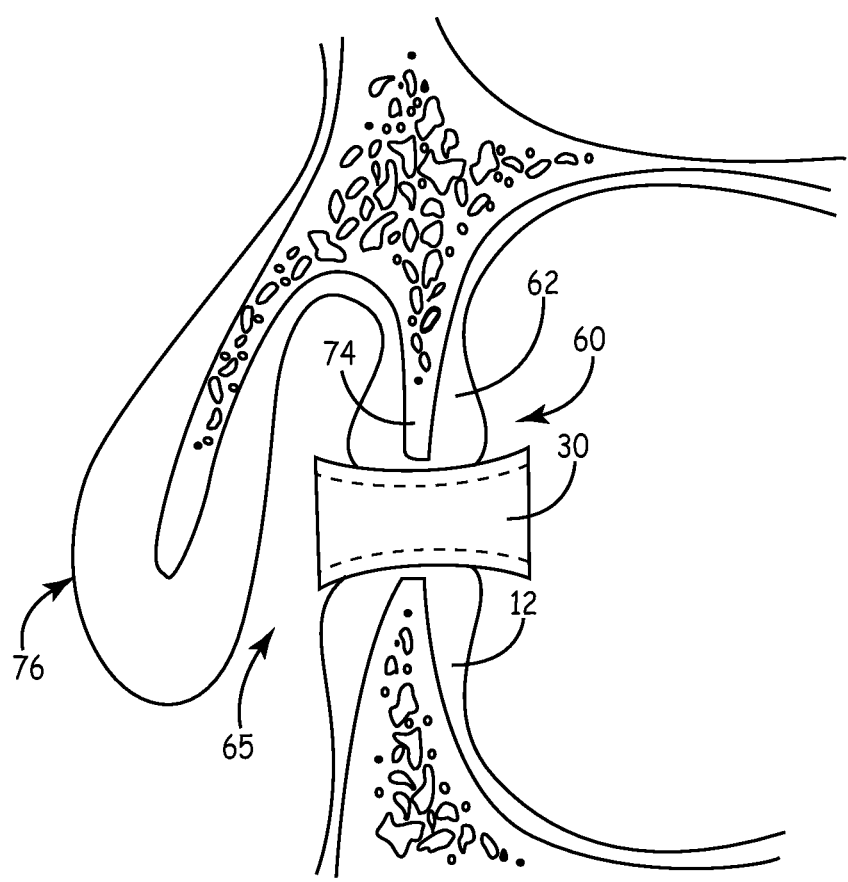
FIG. 5 illustrates a stent according to an embodiment of the present invention in position after placement between the sinus cavity and the nasal cavity.

FIG. 5 shows the sinonasal stent 30 in position after placement and removal of guidewire 52, catheter 54, and balloon 56. When deployed, sinonasal stent 30 provides a constant expansile pressure against mucosa 62 and bone 74 of the sinus opening with clear communication with nasal cavity 65. In addition, adjacent sinus anatomy 76 remains normal, intact, and unimpeded from its function by sinonasal stent 30.

Figure 6A:
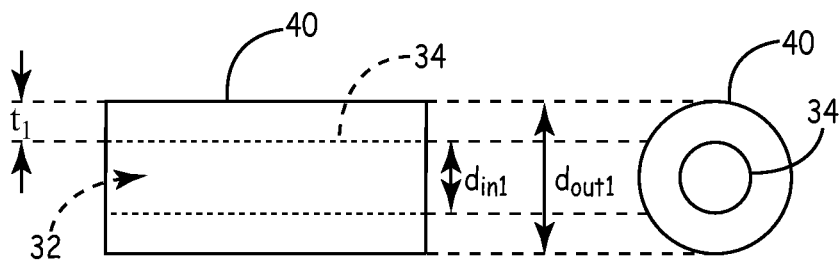
FIG. 6A is a schematic view of the stent device illustrating a thickness of the stent material in an initial state before deployment.
Figure 6B:
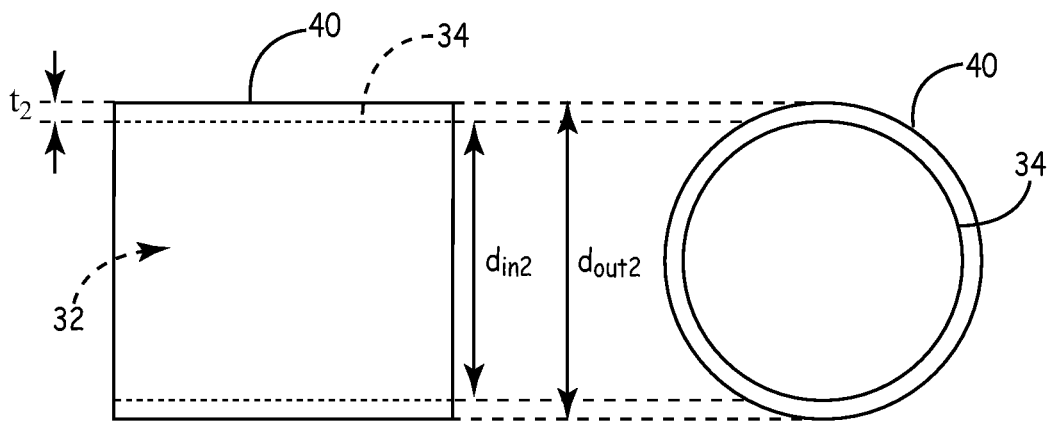
FIG. 6B is a schematic view of the stent device illustrating a thickness of the stent material in a deployed stent device.

FIG. 6A is a schematic view of sinonasal stent 30 in an initial state before deployment, and FIG. 6B is a schematic view of sinonasal stent 30 after deployment. Both FIGS. 6A and 6B illustrate side and axial views of sinonasal stent 30. The schematics of FIGS. 6A and 6B are provided to illustrate the thickness of the stent material before and after deployment, but do not necessarily illustrate the actual shape of sinonasal stent 30 in these states. As shown in FIG. 6A, prior to deployment, sinonasal stent 30 has material thickness $t_1$, inner diameter $i_{in1}$, and outer diameter $i_{out1}$. As shown in FIG. 6B, after deployment sinonasal stent 30 has material thickness $t_2$, inner diameter $i_{in2}$, and outer diameter $i_{out2}$.

Prior to deployment (FIG. 6A), material thickness $t_1$ of sinonasal stent 30 is sufficient to allow integrity of outer stent wall 38 to be maintained after full expansion and deployment. In addition, initial wall thickness $t_1$ is such that, when expanded, deployed wall thickness $t_2$ is sufficient to allow sinus drainage through lumen 32 while maintaining adequate structural integrity for stenting purposes. Initial wall thickness $t_1$ of sinonasal stent 30 may also be determined by, for example, the minimum post-expansion wall thickness $t_2$ needed to maintain outward expansion, the compressibility of the material of sinonasal stent 30, and the minimum inner diameter $i_{in1}$ needed to accommodate a deployment device.

After deployment (FIG. 6B), the selected materials for sinonasal stent 30 retain the properties of an elastomer to provide outward radial pressure on the ostium during early healing. It is important to note that the chosen materials each have the capability of assuming an essentially liquid state at acceptable above-body-temperature so as to avoid not only extensive thermal injury to the patient during deployment, but also to avoid elastic effect during expansion and insertion of sinonasal stent 30. Elasticity during expansion would have the undesirable effect of stent shrinkage after deployment.

In some embodiments, the minimum deployed diameter $i_{out2}$ of sinonasal stent 30 is approximately 6 mm, based upon surgical experience. To maintain the integrity of inner wall 34 and outer wall 40, deployed wall thickness $t_2$ of minimum 1 mm may be used. Current deployment balloons have an outer undeployed diameter of approximately 2 mm. To achieve a final outer diameter $i_{out2}$ of 6 mm and a serviceable inner diameter $i_{in2}$ of 4 mm for drainage and viewing of the sinus cavities beyond sinonasal stent 30 with a typical endoscope, a pre-deployment stent wall thickness $t_1$ of at least 1.5 mm may be used.

Figure 7A:
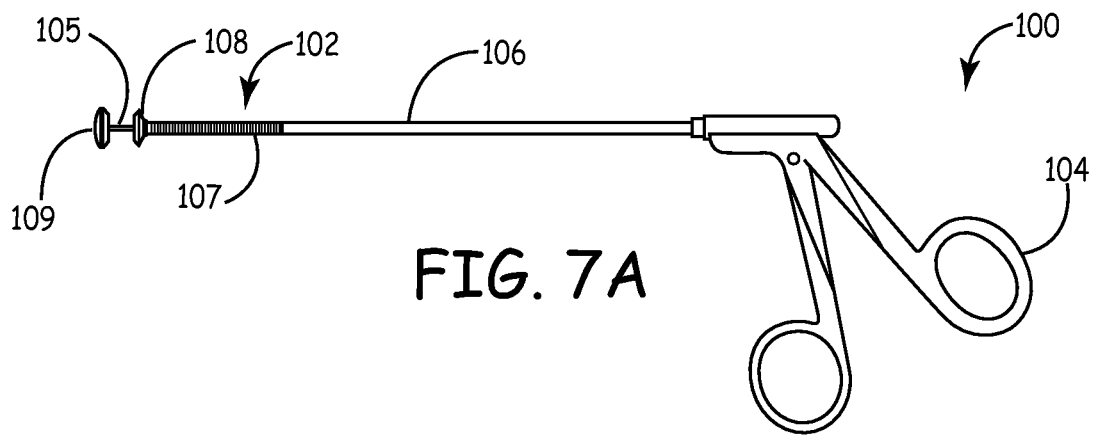
FIG. 7A is a plan view of an insertion device instrument coupled to a stent delivery portion having a straight tip configuration.
Figure 7B:
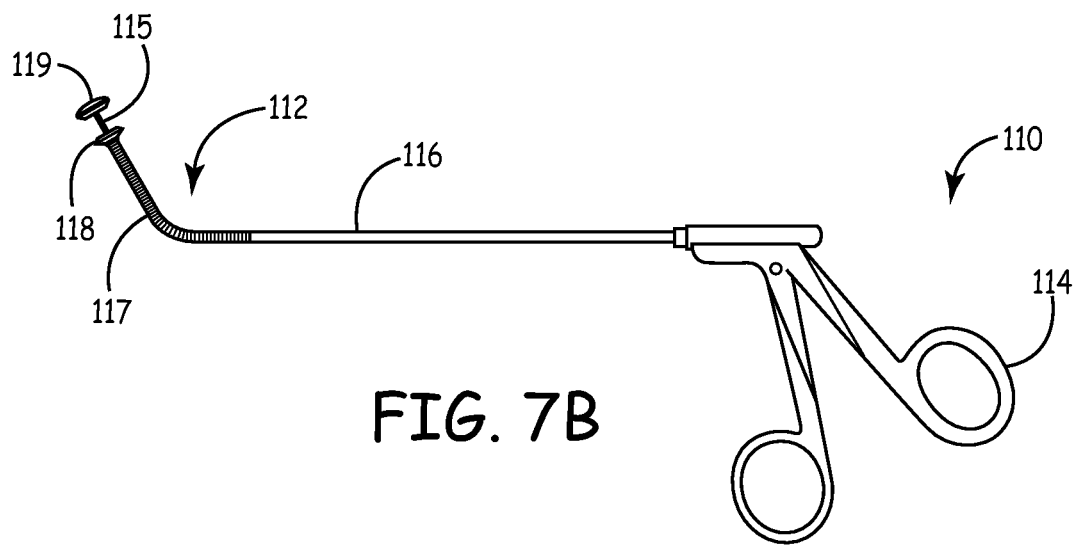
FIG. 7B is a plan view of an insertion device instrument coupled to a stent delivery portion having an obtusely angled tip configuration.
Figure 7C:
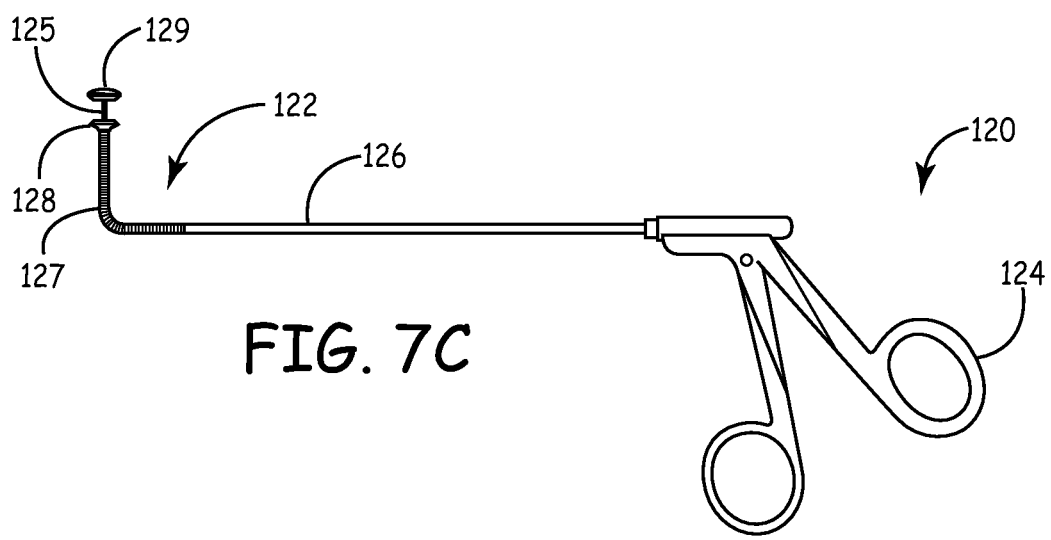
FIG. 7C is a plan view of an insertion device instrument coupled to a stent delivery portion having a substantially right angled tip configuration.
Figure 8A:
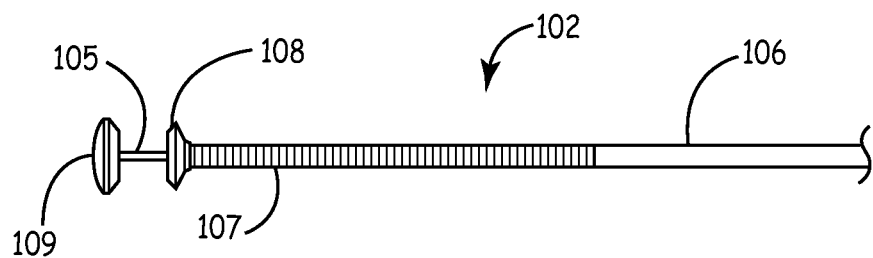
FIG. 8A is a plan view of a distal end of the stent delivery portion shown in FIG. 7A.
Figure 8B:
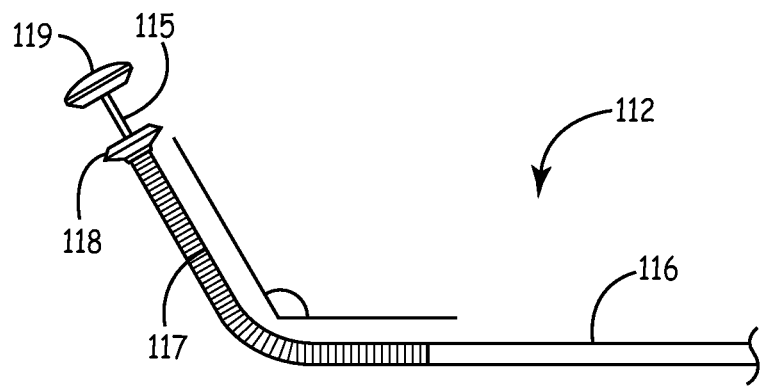
FIG. 8B is a plan view of a distal end of the stent delivery portion shown in FIG. 7B.
Figure 8C:
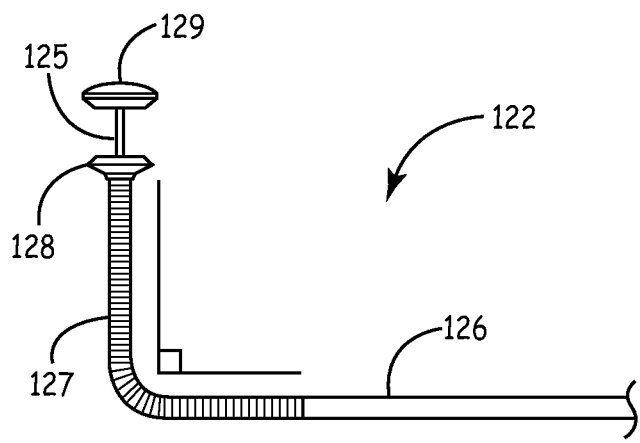
FIG. 8C is a plan view of a distal end of the stent delivery portion shown in 7C.

While delivery of sinonasal stent 30 has been described with regard to use of guidewire 52, catheter 54, and balloon 56, other tools or devices may be used to deliver sinonasal stent 30. For example, FIGS. 7A, 7B, and 7C illustrate devices that may be used to position, insert, and deploy the sinonasal stent 30, according to embodiments of the present invention. In particular, FIG. 7A is a plan view of insertion device 100 coupled to stent delivery portion 102 having a straight distal end, FIG. 7B is a plan view of insertion device instrument 110 coupled to stent delivery portion 112 having an obtusely angled distal end, and FIG. 7C is a plan view of insertion device instrument 120 coupled to stent delivery portion 122 having a substantially right angled distal end. FIG. 8A is a plan view of the straight distal end of stent delivery portion 102, FIG. 8B is a plan view of obtusely angled distal end of stent delivery portion 112, and FIG. 8C is a plan view of substantially right angled distal end of stent delivery portion 122. While the following discussion is directed to the components and functionality of insertion device 100, the components and functionality of insertion devices 110 and 120 are substantially similar, unless otherwise noted. In addition, similar features to those described with regard to insertion device 100 are similarly numbered for insertion devices 110 and 120.

Insertion device 100 includes forceps-like handle 104 which, when actuated, slides wire 105 within shaft 106. In some embodiments, shaft 106 has a length of about six inches (152.4 mm). At the end of the straight portion of shaft 106, a welded stainless steel hollow spring 107 with a memory shape may be coupled, according to embodiments of the present invention. Spring 107 is straight and springs 117 and 127 are angled to facilitate access to various parts of the sinus. That is, spring 107 has a straight configuration, which is suitable for positioning of sinonasal stent 30 into the sphenoid sinus, for example. Spring 117 has an obtusely angled configuration (e.g., 120.degree.), which is suitable for positioning of sinonasal stent 30 into the frontal sinus, for example. Spring 127 has a substantially right angled configuration, which is suitable for positioning of sinonasal stent 30 into the maxillary sinus ostium, for example. Springs 107, 117, and 127 allow malleability and flexibility of the tip of instruments 100, 110, and 120, respectively, to accommodate variation in anatomy from one patient to another. According to some embodiments of the present invention, springs 107, 117, and 127 are shapeable by the surgeon to customize the spring for sinus access in the anatomy of a particular patient.

According to some embodiments of the present invention, moving forceps-like handles 104 of the instrument 100 open and closed moves wire 105 within shaft 106. Lower lip 108 may be formed or attached to spring 107 and/or shaft 106, and upper lip 109 may be formed or attached to wire 105. Moving the forceps-like handles 104 of the instrument 100 open and closed thus moves upper lip 109 towards and away from lower lip 108, respectively, according to embodiments of the present invention.

Figure 9A:
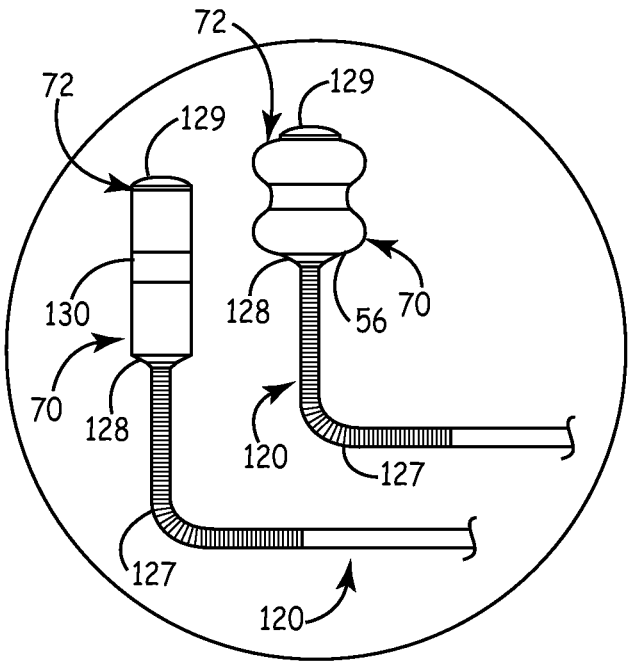
FIG. 9A is a plan view of an exemplary stent delivery portion according to an embodiment of the present invention in both contracted insertion and expanded deployment configurations without the thermally expansile stent in place.

To illustrate methods for using of insertion devices 100, 110, and 120, FIG. 9A is a plan view of an insertion device 120 as shown in FIGS. 7B and 8B with balloon 56 in both contracted and expanded configurations. While the following discussion focuses on the use of insertion device 120, it will be appreciated that the principles described are also applicable to insertion devices 100 and 110.

As shown in FIG. 9A, balloon 56 may be held, clipped, or otherwise secured between the upper lip 129 and the lower lip 128. Sleeve 130 may be placed over the balloon 56 and either adhered and/or pressure fit and/or otherwise secured in place over a middle section of balloon 56. In some embodiments, balloon 56 extends between upper lip 129 and lower lip 128 in a substantially cylindrical configuration. The substantially cylindrical configuration of balloon 56 may have a diameter similar to the inner diameter of the sleeve 130, as shown by the contracted configuration of insertion device 120 in FIG. 9A.

When the distance between upper lip 129 and lower lip 128 is reduced, such as, for example, by either squeezing together or separating handles 124 of instrument 120, balloon 56 expands in diameter as shown in contracted configuration of insertion device 120 in FIG. 9A. Sleeve 130 may be made of a material which is less elastic than the material of balloon 56, such that a middle section of the balloon 56 is restricted from expanding to the same diameter as the ends 70 and 72 of the balloon 56, which gives the balloon 56 a substantially hourglass-shaped configuration. In some embodiments, sleeve 130 is integral with balloon 56.

Figure 9B:
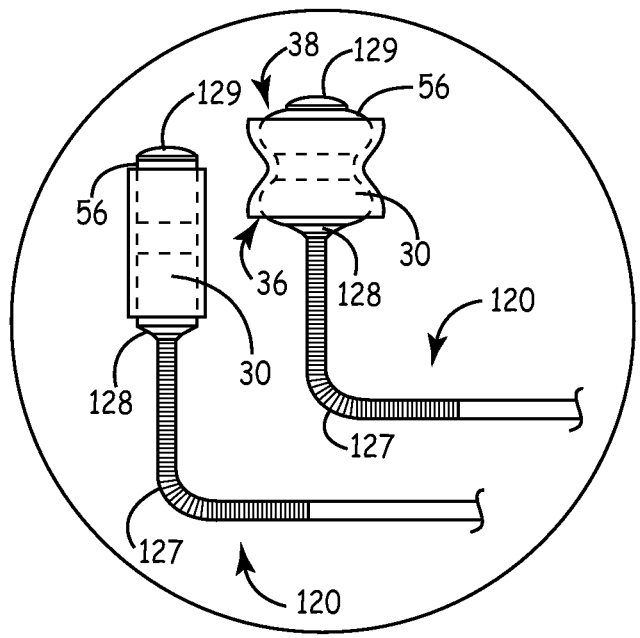
FIG. 9B is a plan view of an exemplary stent delivery portion according to an embodiment of the present invention in both contracted insertion and expanded deployment configurations with the thermally expansile stent in place.

FIG. 9B is a plan view of insertion device 120 with thermally expansile sinonasal stent 30 disposed over balloon 56 in both contracted and expanded configurations. As described above, sinonasal stent 30 may be deformable, elastic, and/or heat activated to conform sinonasal stent 30 to the shape of balloon 56, in order to impart sinonasal stent 30 with a substantially hourglass-shaped configuration. FIG. 9B illustrates sinonasal stent 30 and underlying balloon 56 in an insertion (i.e., contracted) position and also in a deployment (i.e., expanded) position, according to embodiments of the present invention.

Thus, according to some embodiments of the present invention, insertion devices 100, 110, or 120 may be used to place and insert sinonasal stent 30 into the appropriate position, for example in the sinus, while sinonasal stent 30 and balloon 56 are in the contracted position. Insertion devices 100, 110, or 120 may then be used to expand balloon 56 to conform sinonasal stent 30 to the proper size and shape, and/or to otherwise conform sinonasal stent 30 to the geometry of surrounding tissue, as depicted in FIGS. 3 and 4. Once sinonasal stent 30 has been placed and expanded and/or shaped, balloon 56 may be returned to the contracted insertion position while leaving sinonasal stent 30 in place, and insertion device 100, 110, or 120 and balloon 56 may be withdrawn.

In some embodiments, balloon 56 has an outer diameter of approximately 4 mm and the distance between upper lip 129 and lower lip 128 is approximately 12 mm in the contracted insertion position. In some embodiments, balloon 56 has an outer diameter at ends 70 and 72 of approximately 8 mm and the distance between the upper lip 129 and lower lip 128 is approximately 8 mm in the expanded deployed position. Sinonasal stent 30 after deployment may have an outer diameter of approximately eight millimeters toward ends 36 and 38, and approximately 6 mm in the middle, corresponding to the inner diameter of the sinus ostium, according to embodiments of the present invention. As discussed above, balloon 56 may be comprised of an expansile elastomer. These insertion procedures may be viewed by endoscopic examination of the nasal cavity and sinuses.

In some embodiments, lower lip 128 may be a collet, for example a 4 mm diameter metallic disc. Balloon 56 may be an elastomer cylinder with a minimal inner diameter of just slightly larger than shaft 126, such as, for example, approximately 1.5 millimeters. According to some embodiments of the present invention, shaft 126 passes through balloon 56 and is welded into upper lip 129. Upper lip 129 may be, for example, another disc. When handles 124 are actuated, balloon 56 is compressed in length and widened in diameter and circumference to expand sinonasal stent 30 into position, according to embodiments of the present invention.

Figure 10:
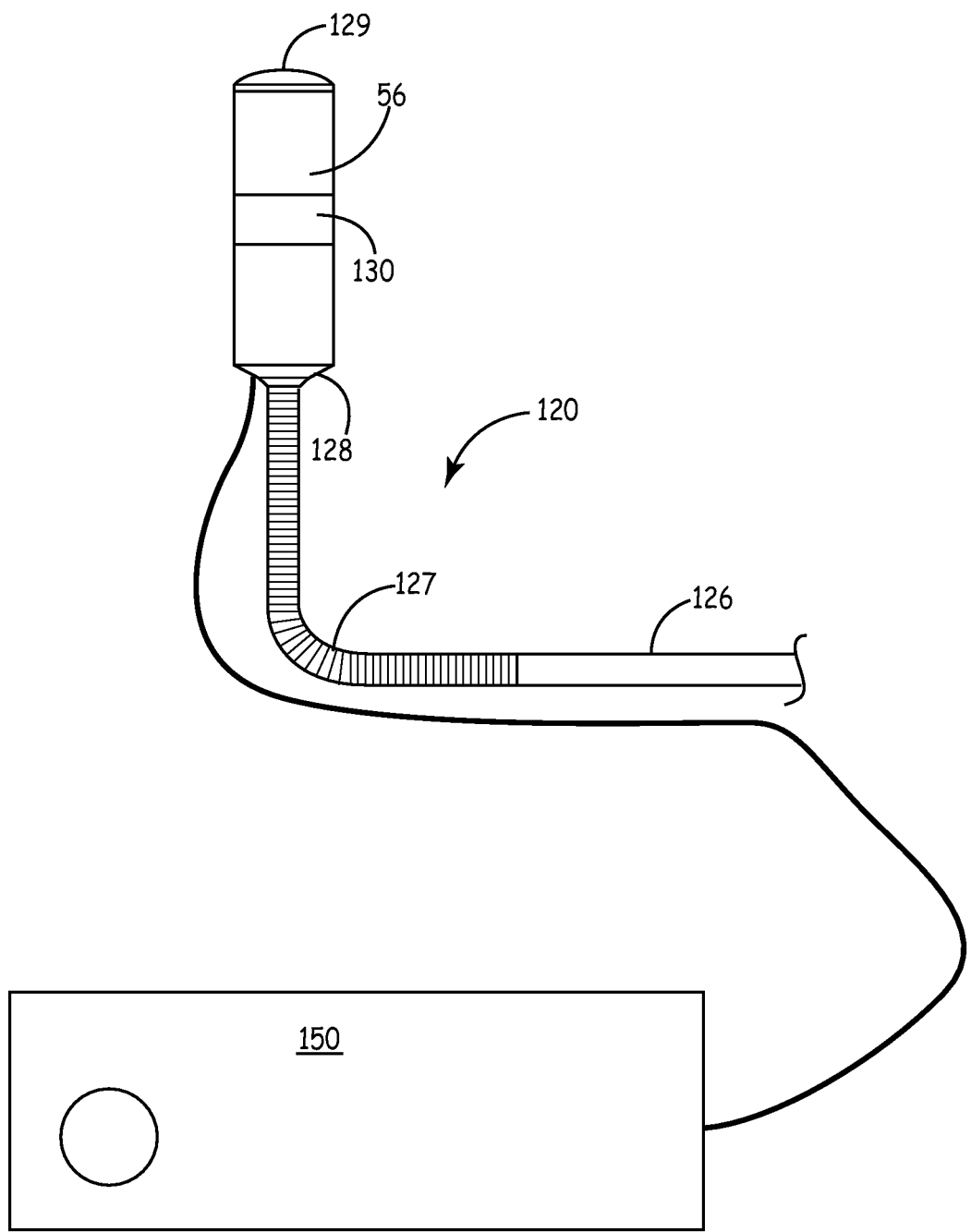
FIG. 10 is a schematic view of heating element control coupled to a stent delivery portion according to the present invention.

FIG. 10 is a schematic view of heating element control 150 coupled to stent delivery portion 122 of insertion device 120, according to the present invention. FIG. 10 illustrates insertion device 120 in one configuration that allows monopolar electric current to be passed through insertion device 120. Heating element 152 may be inserted balloon 56 as shown, and/or may be incorporated within shaft 126, according to embodiments of the present invention. If wire 125 that runs through balloon 56 is a resistive element, current applied to insertion device 120 by heating element control 150 through heating element 152 can be utilized to warm the elastomer of balloon 56 to avail the use of thermal plastic properties of the material of sinonasal stent 30. This can allow in-situ melting and cooling of sinonasal stent 30 at sinus ostium 58, a specific advantage in solving the problem of constant outward radial force from sinonasal stent 30 applied to counteract the constant centripetal force of scar tissue formation in the healing of sinus ostium 58, according to embodiments of the present invention.

According to some embodiments of the present invention, balloon 56 is of a bimaterial nature. That is, the inner part of balloon 56 may be made with a stronger, non-melting material and the outer part of balloon 56 may be made with a different material having a lower durometer and being more pliable.

EXAMPLES

The following Examples are included to demonstrate preferred embodiments of the invention. It should be appreciated by those of skill in the art that the techniques disclosed in the Examples which follow represent techniques discovered to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Sinonasal stent 30 is of use both intraoperatively after surgical opening of a sinus cavity and postoperatively in a clinic setting. Office use of the device may eventually predominate, since most surgical procedures, particularly those done in the primary setting, are assumed by the operating surgeon to be intrinsically successful. Early postoperative failures (within 6 weeks) are common, however, and slow postoperative progression of disease happens frequently.

Example 1

For formation of sinonasal stent 30, the materials noted above for longer indwelling time may be of preferential use in certain disease states—for instance in the case of severe nasal polyposis or when chronic disease states such as cystic fibrosis or inverted papilloma, a type of intranasal neoplasm, are treated. Sinonasal stent 30 as described above and illustrated in FIGS. 2-5 is prepared for insertion into a sinus ostium.

Surgery to expose and open a complicated and/or tortuous frontal sinus opening often results in a lengthy segment of denuded bone. This may occur either from presurgical disease causing weakening of the mucosal lining in the region or may be required by the extent of surgery necessary to find and create an opening. The surgeon expects that normal wound healing processes in the sinus and nose will eventually likely lead to at least partial closure of this opening. Sinonasal stent 30 is placed into the sinus opening to prevent later revision surgery or extensive reworking of the area in the office at follow-up. The stent is then removed after a few weeks, generally when the patient complains of fullness or discomfort in the area. Alternatively, a gradual, planned period of degradation of the stent occurs in situ, eliminating the need to remove the implanted stent.

In other alternatives, sinonasal stent 30 is impregnated with one or more of the therapeutic agents listed above to facilitate the healing process and further inhibit closure of the ostial opening.

Example 2

Many sinus surgeons conduct interval examination of patients with chronic inflammatory disease in the nose. These patients may or may not have had previous surgery. Endoscopic examination of the nose reveals a purulent drainage from a particular sinus or a similar disease process such as an isolated polyp obstructing a sinus. The introducing technique depicted in FIG. 3 can be used to identify the opening into the sinus. The opening may be widened to a functional caliber either by means of conventionally used punches or with the expansion of balloon 56 and sinonasal stent 30 across its ostium. Sinonasal stent 30 may later degrade or be withdrawn, obviating the need for major surgical procedure. Sinonasal stent 30 is composed of the same material as that in Example 1—a device with a usable life of approximately 6 weeks.

Example 3

Many patients suffer from aggressive pansinus polyposis due to, for example, asthma-like conditions in their nasal tissues, aspirin-sensitivity disorders, or other similar conditions. These patients have a much more futile problem in many respects than those in Examples 1 and 2. They are often expected to have recurrence of their disease and become the subject of multiple, serial surgical procedures. Without the constant application of pharmaceuticals, generally in the form of surfactants, high potency steroids, or diuretic solutions, the polyps reform. Similar problems are encountered with the disease state of inverted papilloma which has a high tendency of recurrence and a risk of malignant transformation. These disease states would better be treated with pansinus stenting preemptively at the time of surgery with as long a dissolution time in stent wall 40 as allowable for elution of a drug. This would favor the use of any of the stent material compounds listed in Table 1 or the materials suitable for longer indwelling time listed above.

In summary, the present invention relates to methods, compositions and apparatuses for treating chronic and/or recurring acute inflammatory and infectious conditions of the nose and paranasal sinuses. Certain embodiments may concern a stent device that is implantable into the nose, paranasal sinuses or sinus ostia. In some embodiments, the stent is made from material of a customizable shape, which may be biocompatible, dissolvable, retrievable, and/or drug-elution capable or some combination thereof. The stent may dissolve over a predetermined and variable schedule, may be impregnated with one or more selected therapeutic compounds, and may be easily removed at the discretion of the treating physician.

In various embodiments, the stent comprises a material that is formed prior to insertion by partial melting with heat or chemical alteration. In some embodiments, the chemical composition of the material allows the melting to be repeated to allow for nondestructive removal of the device. Such heat deformable materials are well known in the art and any such known material may be used. Alternatively, the stent may comprise a coated metal or polymer that exhibits a "memory" characteristic, such that the size and shape of the stent may be manipulated between alternative conformations for ease of insertion and/or removal.

Other embodiments may concern catheters of use for inserting the stent device into a selected sinus location. In some embodiments, such catheters may comprise a guidewire and a hollow directional sheath for localizing and directing the deployment of the device into a selected sinus location.

Still other embodiments may concern methods of treating a patient with a sinus disease, comprising obtaining a stent device as discussed herein and inserting the device into the nose, the paranasal sinuses or the sinus ostia of the patient. The insertion may occur after sinus surgery, to prevent or reduce sinus closure after surgery. Alternatively, the device may be inserted as an alternative to surgery in cases where nasal or sinus closure is not sufficient to require surgical intervention. Preferably, non-surgical intervention with a stent device as described herein may prevent the progression of sinus disease to a point where surgery is required, allowing for non-surgical treatment and/or cure of the sinus condition. The use of stent devices comprising one or more therapeutic agents further contributes to treatment.

The sinonasal stent of the present invention exhibits significant advantages over previously known methods and devices. The described device is conformable to the irregular geometry of the nasal and sinus passages, exhibits sufficient outward pressure to counteract fibroblast contraction, may comprise a variety of therapeutic agents for sustained release to treat or prevent inflammation, infection and/or scarring, may comprise a self-centering geometry to maintain the position of the device in the sinus ostia, is designed for ease of insertion and/or removal, and may alternatively be comprised of a material that dissolves in situ in the sinus, obviating the need for removal of the inserted stent device. The claimed device provides a stent design that is employable under direct endoscopic guidance owing to a small insertion diameter. Once delivered to the sinus to be treated, the stent can be expanded by balloon inflation or other methods to conform directly to the topography of the ostium.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

What is claimed is:

1. A method of maintaining a patent paranasal sinus ostium passageway between a sinus and a nasal cavity, the method comprising:
   providing a tubular element extending longitudinally from a proximal end, through a center region, and to a distal end;
   delivering the tubular element in an insertion state to the sinus ostium passageway such that the center region is disposed in the sinus ostium passageway, the distal end is disposed in the sinus, and the proximal end is disposed in the nasal cavity, wherein the tubular element has a maximum outer diameter in the insertion state, and the maximum outer diameter in the insertion state is equal to or larger than a diameter of the sinus ostium passageway; and
   expanding the tubular element from the insertion state to a deployment state, wherein, in the deployment state, the center region confronts a wall of the sinus ostium passageway with an outward radial force configured to define a maximum diameter of the sinus ostium passageway, the proximal end extends beyond the maximum diameter of the sinus ostium passageway into the sinus, and the distal end extends beyond the maximum diameter of the sinus ostium passageway into the nasal cavity.

2. The method of claim 1, further comprising:
   prior to the expanding and in the insertion state, heating the tubular element to an above-body temperature at which the tubular element partially melts to allow reshaping of the tubular element from the insertion state to the deployment shape; and after the expanding and in the deployment state, cooling the tubular member into a solid state having integrity at a body temperature of less than the above-body temperature.

3. The method of claim 1, wherein the tubular element comprises a material that is at least partially meltable.

4. The method of claim 3, wherein the material has a melting point of less than 100° C.

5. The method of claim 1, wherein the tubular element comprises a material that incorporates a therapeutic agent.

6. The method of claim 1, wherein the tubular element comprises a material that dissolves within approximately one year.

7. The method of claim 1, wherein the tubular element comprises a material selected from a group consisting of poly-ε-caprolactone, polyhydroxybutyrate, poly-4-hydroxybutyrate, polyglycolic acid, polhydroxypropionate, polyhydroxyvalerate, polybutyrolactone, polyglycolic acid, hyaluronic acid in resin form, poly-4-hydroxybutyrate, crosslinked hyaluronic acid, porcine collagen in resin form, methylmethacrylate, cyanoacrylate, polybutylmethacrylate, poly(L-lactide) and poly(D-lactide), polybutylmethacrylate, and polyethylene covinyl acetate.

8. The method of claim 1, wherein, in the deployment state, the center region has diameter that is less than a diameter than at least one of the proximal end and the distal end.

9. The method of claim 1, wherein, in the deployment state, the tubular element has an hourglass shape.

10. The method of claim 1, wherein the center region is comprised of a first material and a remainder of the tubular element is comprised of a second material different than the first material.

11. The method of claim 1, wherein a wall thickness of the tubular element is smaller in the deployment state than in the insertion state.

12. A method for maintaining a passageway from a sinus to a nasal cavity through a sinus ostium containing obstructive soft tissue, the method comprising:
configuring a tubular element in an insertion state, the tubular element having a proximal end, a distal end, and a center region therebetween, wherein the tubular element has a maximum outer diameter in the insertion state, and the maximum outer diameter in the insertion state is equal to or larger than a diameter of the sinus ostium;
using the tubular element in the insertion state, displacing the obstructive soft tissue to deliver the tubular element to the sinus ostium such that the distal end is disposed in the sinus, the proximal end is disposed in the nasal cavity, and the center region is disposed in the sinus ostium; and
expanding the tubular element from the insertion state to a deployment state such that the center region of the tubular confronts the sinus ostium with a constant outward radial force that counteracts a centripetal force of the obstructive soft tissue and defines a maximum diameter of the passageway through the sinus ostium.

13. The method of claim 12, wherein the expanding comprises:
partially melting the tubular element to allow reshaping of the tubular element from the insertion state to the deployment state;
enlarging the tubular element from the insertion state to the deployment state; and
cooling the tubular element to a body temperature at which the tubular element is a solid in the deployment state.

14. The method of claim 12, wherein, in the deployment state, the proximal end extends beyond the maximum diameter of the passageway into the sinus, and the distal end extends beyond the maximum diameter of the passageway into the nasal cavity.

15. The method of claim 14, wherein, in the deployment state, the tubular element has an hourglass shape.

16. The method of claim 12, wherein the center region of the tubular element is comprised of a first material and a remainder of the tubular element is comprised of a second material different than the first material.

17. The method of claim 12, further comprising:
dissolving the tubular element within approximately one year to leave the passageway in a healed state.

18. The method of claim 12, wherein the tubular member continuously releases a therapeutic agent into the sinus ostium.

19. A method for maintaining a passageway from a sinus to a nasal cavity through a sinus ostium containing obstructive soft tissue, the method comprising:
providing a tubular element having a proximal end, a distal end, and a center region therebetween;
delivering, in an insertion state, the tubular element to the sinus ostium such that the center region is disposed in the sinus ostium, the distal end is disposed in the sinus, and the proximal end is disposed in the nasal cavity, wherein the tubular element has a maximum outer diameter in the insertion state, and the maximum outer diameter in the insertion state is equal to or larger than a diameter of the sinus ostium;
heating the tubular element to an above-body temperature at which the tubular element partially melts to allow reshaping of the tubular element;
expanding the tubular member from the insertion state into a deployment state in which the center region confronts the sinus ostium with an outward radial force; and
cooling the tubular member into a solid state having integrity at a body temperature of less than the above-body temperature.

20. The method of claim 19, wherein the center region of the tubular element is comprised of a first material and a remainder of the tubular element is comprised of a second material different than the first material.

* * * * *